US010274485B2

(12) United States Patent
Templin et al.

(10) Patent No.: US 10,274,485 B2
(45) Date of Patent: Apr. 30, 2019

(54) METHOD FOR DETECTING BIOMOLECULES

(75) Inventors: Markus Templin, Tuebingen (DE);
Fridolin Treindl, Geislingen (DE);
Anette Doettinger, Eningen (DE);
Oliver Poetz, Tuebingen (DE)

(73) Assignee: NMI Naturwissenschaftliches und Medizinisches Institut an der Universität Tübingen (DE)

( * ) Notice: Subject to any disclaimer, the term of this patent is extended or adjusted under 35 U.S.C. 154(b) by 770 days.

(21) Appl. No.: 14/235,598

(22) PCT Filed: Jun. 27, 2012

(86) PCT No.: PCT/EP2012/062403
§ 371 (c)(1),
(2), (4) Date: Mar. 25, 2014

(87) PCT Pub. No.: WO2013/013922
PCT Pub. Date: Jan. 31, 2013

(65) Prior Publication Data
US 2014/0248715 A1 Sep. 4, 2014

(30) Foreign Application Priority Data
Jul. 28, 2011 (DE) .................. 10 2011 109 063

(51) Int. Cl.
G01N 31/00 (2006.01)
G01N 33/53 (2006.01)
G01N 33/543 (2006.01)
G01N 33/68 (2006.01)

(52) U.S. Cl.
CPC . *G01N 33/54306* (2013.01); *G01N 33/54313* (2013.01); *G01N 33/6842* (2013.01)

(58) Field of Classification Search
None
See application file for complete search history.

(56) References Cited

U.S. PATENT DOCUMENTS

| 5,948,627 A | 9/1999 | Lee et al. |
| 7,252,954 B2 | 8/2007 | Wang et al. |
| 2003/0013126 A1 | 1/2003 | Singh et al. |
| 2003/0044843 A1 | 3/2003 | Tanaka et al. |
| 2004/0029292 A1 | 2/2004 | Joos et al. |
| 2004/0115834 A1 | 6/2004 | Sloane et al. |
| 2010/0331199 A1 | 12/2010 | Stoll et al. |

FOREIGN PATENT DOCUMENTS

| CN | 1496481 | 5/2004 | | |
| CN | 1563982 | 1/2005 | | |
| CN | 1726394 | 1/2006 | | |
| CN | 101392172 | 3/2009 | | |
| CN | 101416061 | 4/2009 | | |
| CN | 101550441 | 10/2009 | | |
| CN | 101550441 A | * 10/2009 | | |
| CN | 101550447 | 10/2009 | | |
| CN | 101846672 | 9/2010 | | |
| CN | 101550441 B | * 11/2011 | | |
| DE | 603 17 315 | 8/2008 | | |
| WO | 02/075321 | 9/2002 | | |
| WO | WO 02/075321 A1 | * 9/2002 | ............. | G01N 35/00 |
| WO | WO-02075321 A1 | * 9/2002 | ............. | B01L 3/5085 |
| WO | 02/095356 | 11/2002 | | |
| WO | 2003/083476 | 10/2003 | | |
| WO | 2004/027379 A2 | 4/2004 | | |
| WO | 2004/074452 | 9/2004 | | |
| WO | 2007/008084 | 1/2007 | | |
| WO | 2010/057318 A1 | 5/2010 | | |
| WO | 2010/094300 A1 | 8/2010 | | |

OTHER PUBLICATIONS

Nolan et al. (Cytometry A, May 2006, 69(5), pp. 318-325).*
Ernoult et al. (Journal of Biomedicine and Biotechnology, pp. 1-8, 2010).*
Choi et al. (Electrophoresis 2010, vol. 31, pp. 440-447).*
L. Alvarez et al., "Electrophoresis of Native Proteins on Agarose Gels Containing Volatile Buffers," Analytical Letters, vol. 22, No. 13-14, 1989, pp. 2737-2746 (Abstract).
Second Office Action dated Nov. 18, 2015 of corresponding Chinese Application No. 201280047533.4 along with its English translation.
Third Office Action dated Jul. 12, 2016, of corresponding Chinese Application No. 201280047533.4 in English.
English translation of Chinese Office Action dated Jan. 27, 2015 of corresponding Chinese Application No. 201280047533.4.
Meehan, K.L. et al., "Proteomics and the Search for Biomarkers of Female Reproductive Diseases," *Reproduction*, 2010, vol. 140, pp. 505-519.
Xue, G-P., "Characterisation of the DNA-Binding Profile of Barley HvCBF1 Using an Enzymatic Method for Rapid, Quantitative and High-Throughput Analysis of the DNP-Binding Activity," *Nucleic Acids Research*, 2002, vol. 30, No. 15, pp. 1-11.
Öztürk, A. et al., "Proteomic Identification of AP2γ as a Rat Placental Lactogen II Trophoblast Cell-Specific Enhancer Binding Protein," *Endocrinology*, Sep. 2006, vol. 147, No. 9, pp. 4319-4329.
Poetz, O. et al., "Sequential Multiplex Analyte Capturing for Phosphoprotein Profiling," *Molecular & Cellular Proteomics*, 2010, vol. 9, No. 11, pp. 2474-2481.
Hoeppe, S. et al., "Targeting Peptide Termini, a Novel Immunoaffinity Approach to Reduce Complexity in Mass Spectrometric Protein Identification," *Molecular & Cellular Proteomics*, 2011. vol. 10, No. 2, pp. 1-11.
Joos, T.O. et al., "Miniaturised Multiplexed Immunoassays," *Current Opinion in Chemical Biology*, 2001, vol. 6, pp. 76-80.

(Continued)

*Primary Examiner* — Lisa V Cook
(74) *Attorney, Agent, or Firm* — DLA Piper LLP (US)

(57) ABSTRACT

A method of detecting biomolecules present in a complex biological sample includes a) separating the biological sample into fractions according to at least one physical property of the biomolecules; and b) specifically detecting biomolecules present in the fractions using at least one solid-phase-based, immunological detection method including immobilizing the biomolecules from the individual fractions on microsphere populations specific for each fraction and distinguishable from one another.

19 Claims, 9 Drawing Sheets

(56) References Cited

OTHER PUBLICATIONS

Dynabeads® Streptavidin Trail Kit, *Von Invitrogen*, 2007, 2 pages.
German Search Report dated Feb. 28, 2012 from corresponding German Patent Application No. 10 2011 109 063.4.
Notice of Reexamination dated Nov. 16, 2017, of corresponding Chinese Application No. 201280047533.4, along with an English translation.

* cited by examiner

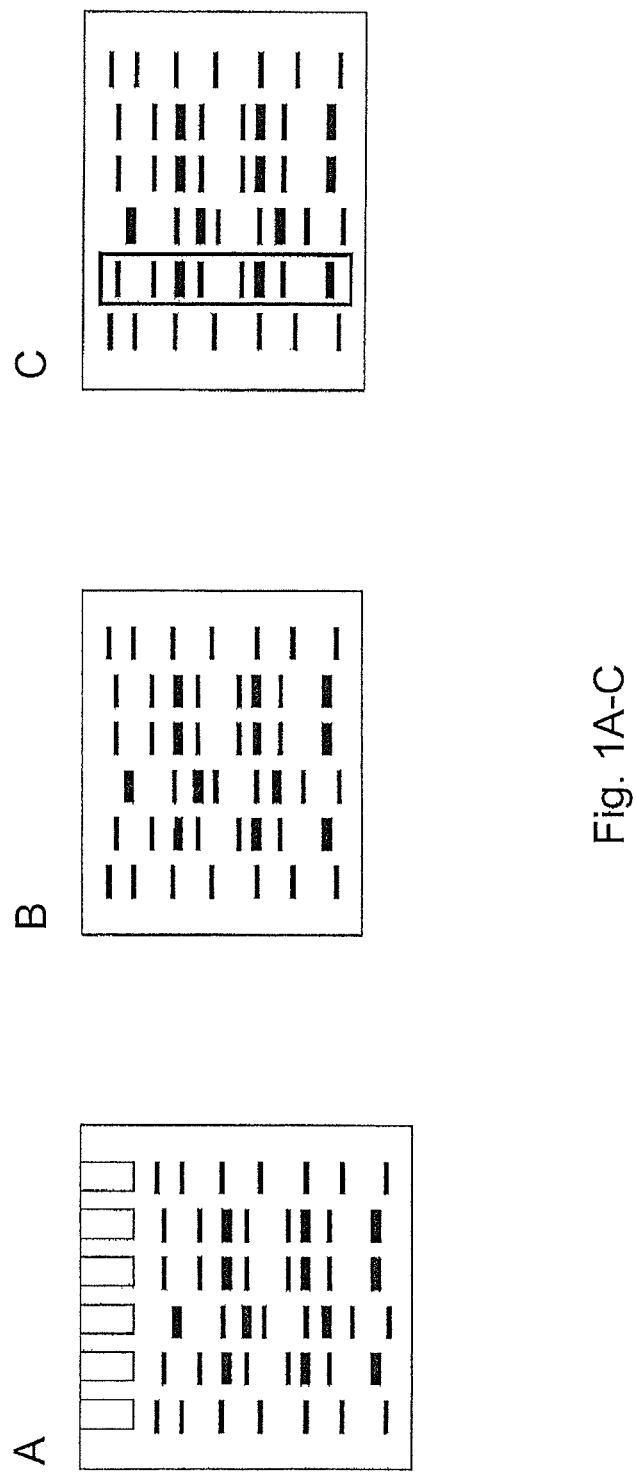
Fig. 1A-C

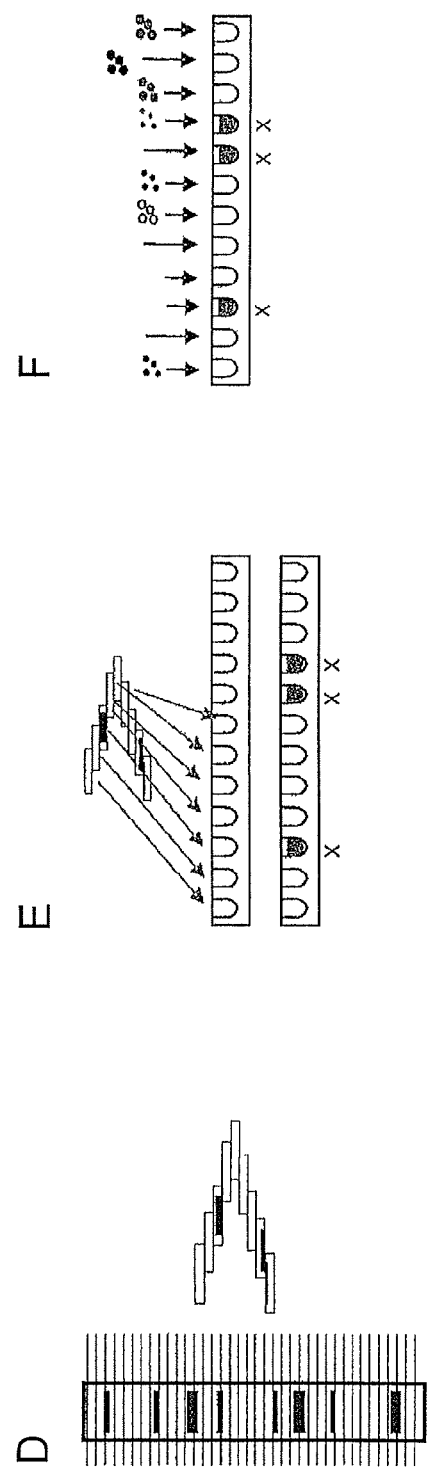
Fig. 1D-F

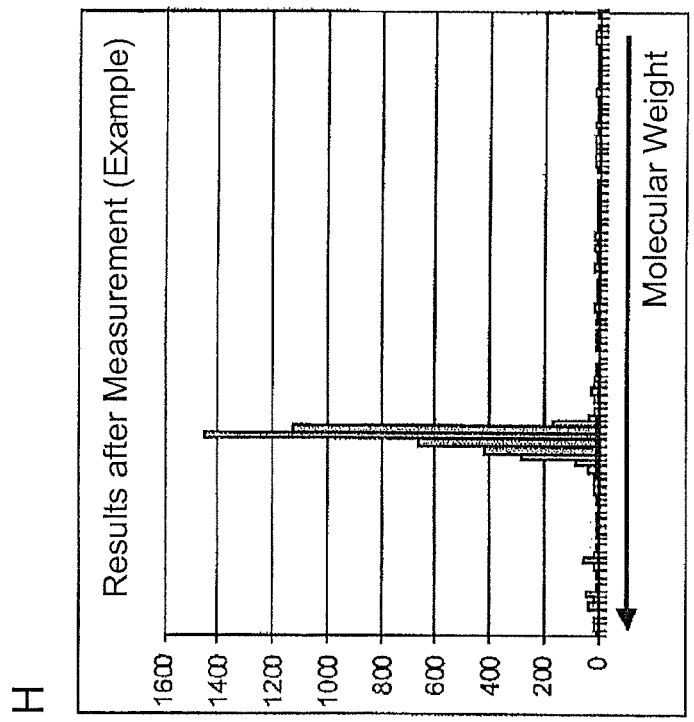
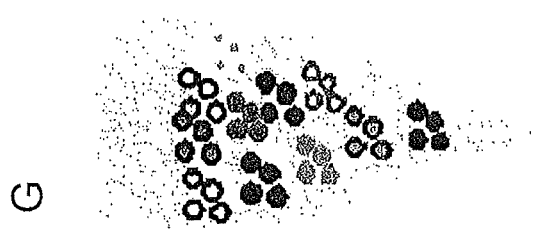
Fig. 1G,H

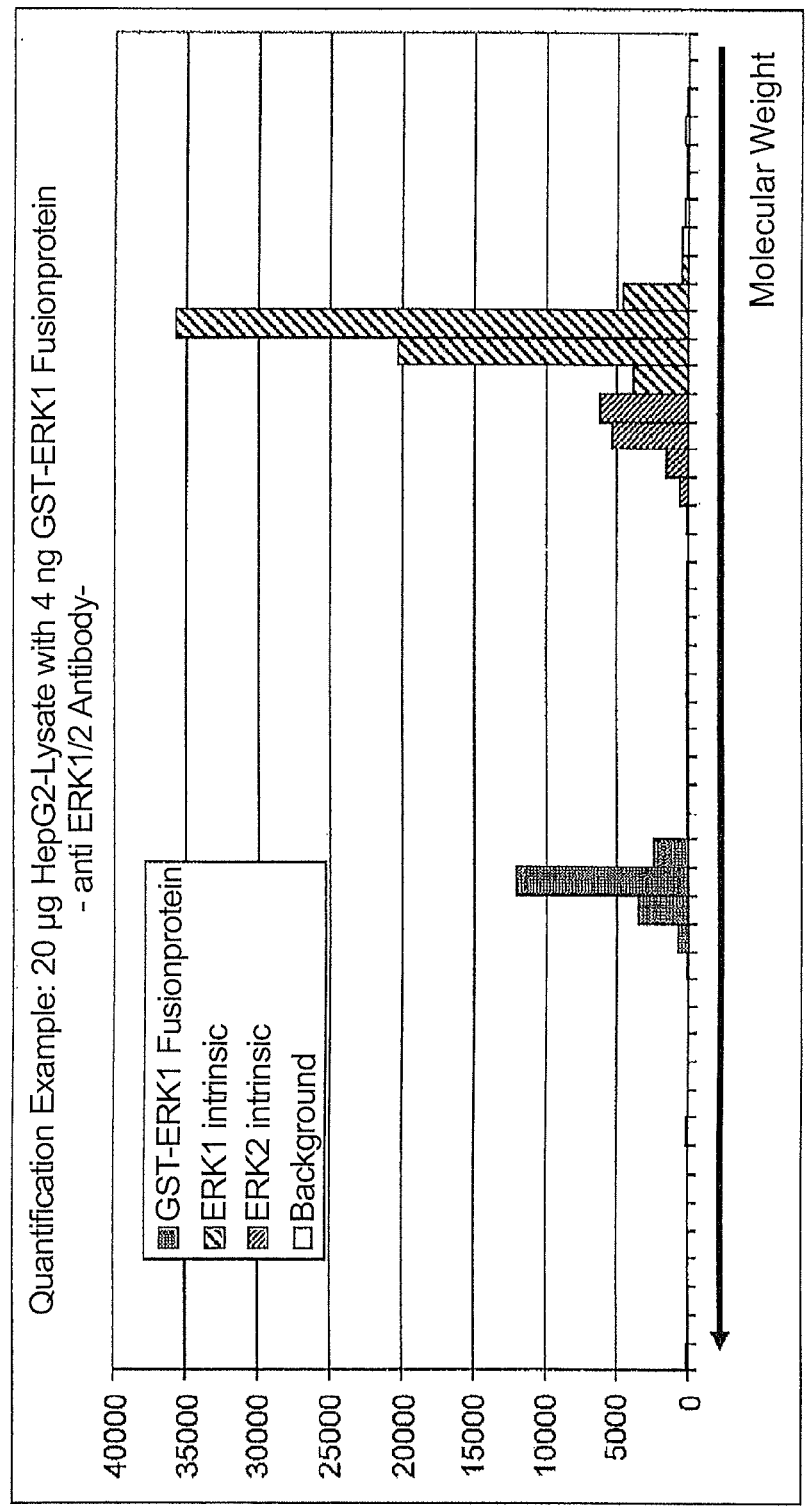

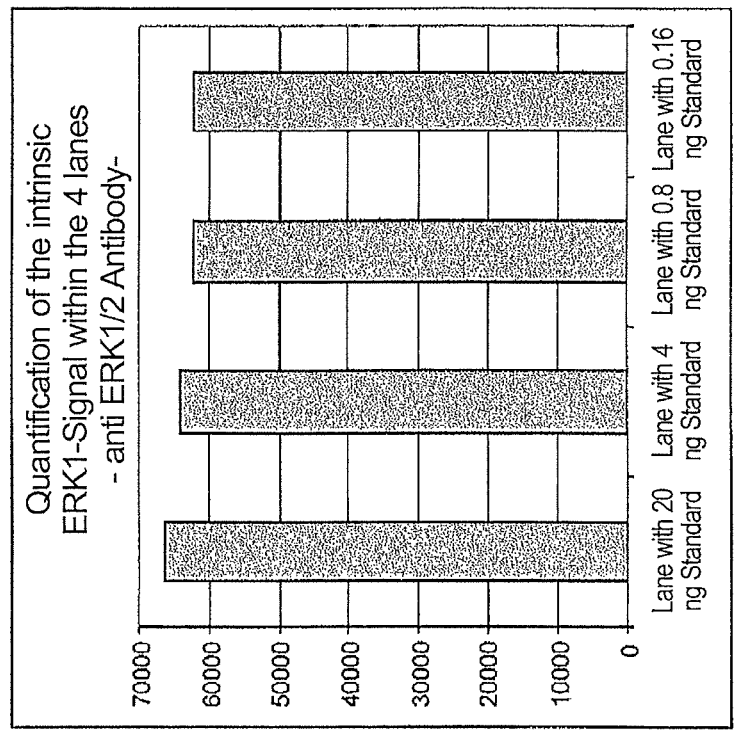
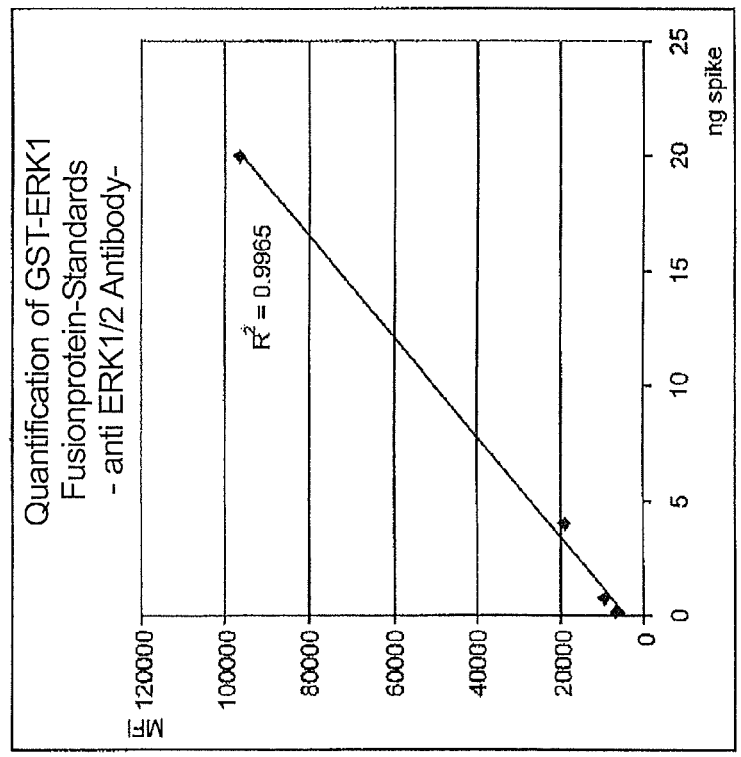
Fig. 3B

METHOD FOR DETECTING BIOMOLECULES

RELATED APPLICATIONS

This is a 371 of International Application No. PCT/EP2012/062403, with an international filing date of Jun. 27, 2012 (WO 2013/013922, published Jan. 31, 2013), which is based on German Patent Application No. 10 2011 109 063.4 filed Jul. 28, 2011.

TECHNICAL FIELD

This disclosure relates to a method which makes it possible to detect biomolecules in biological material, more particularly proteins and/or peptides or proteins digested to form peptides.

BACKGROUND

Methods of this type are widely known.

The specific detection of biomolecules, more particularly of proteins and/or peptides from small amounts of biological material is an important requirement for research and medical diagnostics.

Therefore, the aim of new developments is to increase the sensitivity of known detection methods, more particularly of protein detection methods. More particularly, the aim is to be able to detect and quantify a larger number of different proteins or protein variants at the same time in one sample.

Technological developments which have brought significant advances in the detection of proteins are in particular mass spectrometry and microarray based approaches.

Mass spectrometric methods are capable of detecting a large number of different proteins in an unambiguous manner from a complex sample. Sensitivity is a critical issue with that technology, despite major advances in separation and detection techniques, since the sensitive detection of proteins from small sample amounts is frequently not possible due to system limitations.

A second critical issue is the cost associated with mass spectrometric analysis. To allow specific protein detection, complicated and cost-intensive sample preparation and protein separation techniques are required. Thus, the costs for the equipment required for this purpose, i.e., the actual mass spectrometer, are very high.

The result has been that mass spectrometric analyses are carried out in a few specialized laboratories and only a small portion of the diagnostic detection methods available are based on this technique.

Immunoassays such as immunohistochemistry, direct immunoassay and sandwich immunoassay are, therefore, vastly more important analytical methods in research laboratories and also in clinical analyses. They generally allow the specific detection of proteins in complex samples without complicated sample preparation.

The achievable sensitivity can reach as low as the femtomolar concentration range, and specificity of the measurement signal can be very high.

In recent years, great efforts have been made to bring the immunoassay from the determination of individual parameters into a multiplex format so that it is possible to detect a larger number of different proteins at the same time.

For example, protein microarrays, which in the form of solid-phase assays on planar supports or on microspheres represent a significant miniaturization of immunoassays, have been developed which allow detection and quantification of dozens to hundreds of different proteins from a few microliters of sample volume.

In those antibody-based approaches, a first problem is the lack of binding affinity molecules, i.e., of antibodies, which are a prerequisite for a sensitive and specific immunoassay. A second problem is cross-reactivity of the antibodies used with one another and cross-reactivity with different analyte proteins.

Those limitations frequently result in the sensitivity of the detection method being distinctly lowered when more than about 20 proteins are simultaneously detected.

Immunoblots, also known as Western blots, are also known, which first comprise using gel electrophoresis in a support matrix to separate proteins according to their size, charge or other physical properties into bands and then transferring the bands onto a membrane, where the proteins are then accessible for antibody binding events.

That method is hampered by the same disadvantages as the above-described immunoassays.

In view of the above, it could be helpful to provide a simple and inexpensively implementable method of the type mentioned at the outset, with which it is possible to specifically and sensitively detect from small amounts of biological material a multiplicity of biomolecules, more particularly, proteins, peptides or proteins digested to form peptides.

SUMMARY

We provide a method of detecting biomolecules present in a complex biological sample including a) separating the biological sample into fractions according to at least one physical property of the biomolecules, and b) specifically detecting biomolecules present in the fractions using at least one solid-phase-based, immunological detection method including immobilizing the biomolecules from the individual fractions on microsphere populations specific for each fraction and distinguishable from one another.

BRIEF DESCRIPTION OF THE DRAWINGS

FIGS. 1A to H show individual method steps.

FIGS. 3A and B show two bar charts and a regression curve concerning the quantification of ERK1 in a human liver cell line.

DETAILED DESCRIPTION

Figure 2:
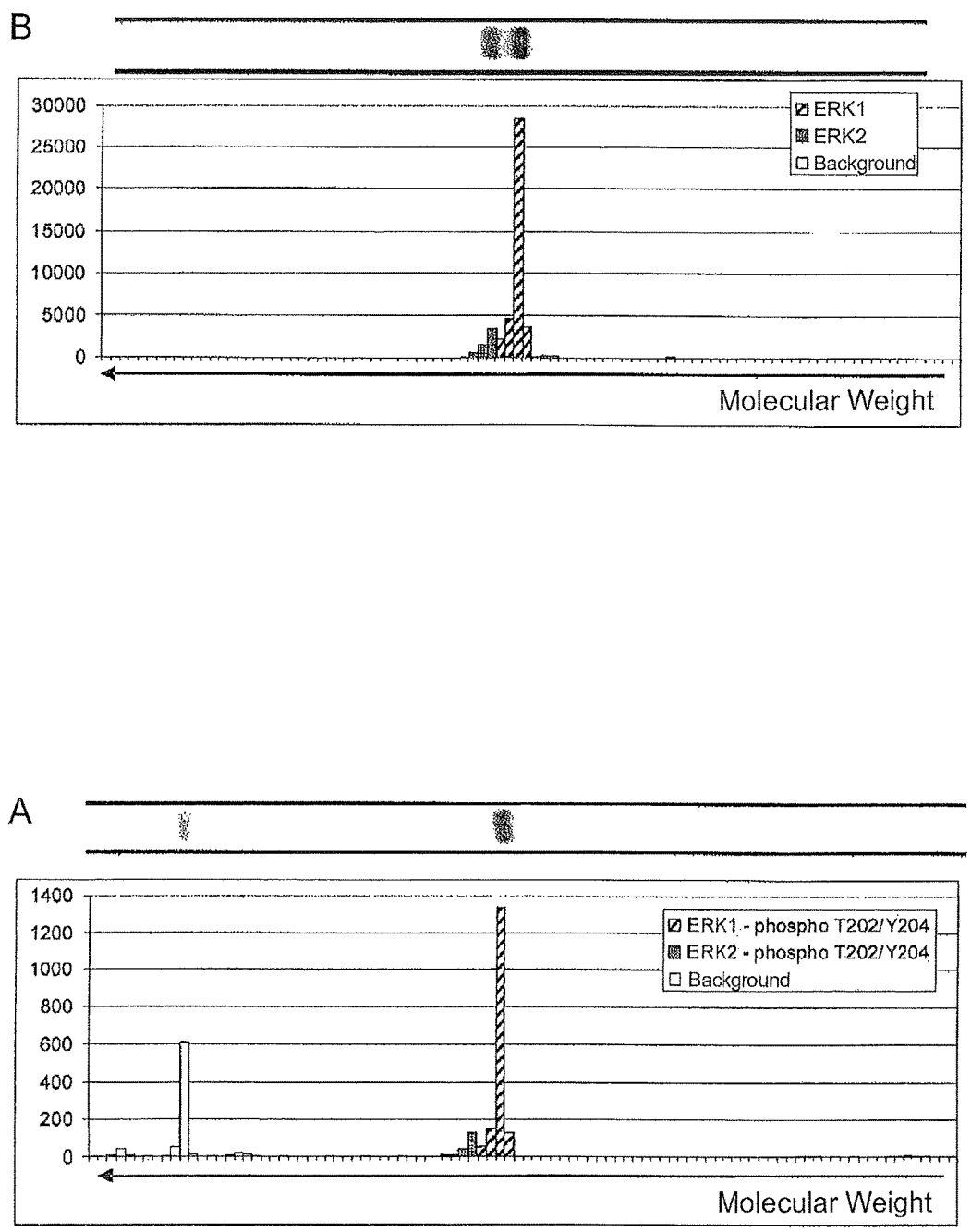
FIGS. 2A and B show two bar charts concerning the detection of ERK1/ERK2 from a human liver cell line.

We provide a method comprising the steps of:
a) separating the biological sample into various fractions according to at least one physical property of the biomolecules; and
b) specifically detecting biomolecules present in the fractions using at least one solid-phase-based, immunological detection method, which involves immobilizing the biomolecules from the individual fractions on microsphere populations which are specific for each fraction and distinguishable from one another.

A "complex biological sample" means a sample containing a mixture of various biomolecules which can be of natural origin or which have been prepared synthetically/by genetic engineering. The sample can also consist of a small amount of tissue, for example, biopsy material or of cultured cells.

Biomolecules mean molecules which originate from a biological sample in the above sense, and are accessible to our methods. More particularly, the biomolecules defined in this way include proteins, peptides and polysaccharides.

Separations in step a) is achieved, for example, by column chromatography and specific detection in step b) is achieved using microspheres.

Therefore, fractionation of the complex biological sample is followed by use of a microsphere-based immunoassay, i.e., a multiplex, miniaturized system to detect hundreds of proteins from a small sample amount in one immunoassay.

The biomolecule separation according to physical property obtained in step a), i.e., the collection of the biomolecules in the fractions representing different physical property values, is "frozen" by the binding of the biomolecules to the microspheres. The assignment of the individual biomolecules to the fractions can, even after mixing the microspheres from some or all fractions, be subsequently retrieved again and/or be used for further analysis, because the microspheres used for different fractions are distinguishable from one another, for example, via their coloring.

Therefore, a physical method is first used to separate the biomolecules, and the fractions obtained are then re-immobilized on different populations of microspheres.

Unexpectedly, immunological analysis is possible after loading the microspheres with unknown biomolecules, more particularly proteins/peptides. Thus, mass spectrometric analysis is not required.

The biomolecules then present accumulated on the microspheres (beads) are detected, for example, in a multiplex immunoassay after mixing the microspheres. For this assay, all bead populations (i.e., all fractions) can be mixed and, at the same time, incubated with one antibody.

The microsphere populations used can, for example, be those from the xMAP® technology of Luminex Corp., Austin, Tex. That technology uses up to 500 differently color-coded microsphere populations or sets which can be individually recognized in an appropriate reader.

For each set of identically coded microspheres, optical signals of the substances bound to the microspheres can be measured and outputted as a summed signal.

If differently color-coded sets of microspheres are loaded with various substances, it is possible in one analytical operation to capture the optical signals for the different sets of identically color-coded microspheres and to present them assigned to the respective set of microspheres.

Therefore, the separation capacity of physical methods such as one-dimensional or two-dimensional gel electrophoresis or isoelectric focussing is combined with the flexibility and detection sensitivity of a bead-based assay system.

In one example of our new methods, all proteins present in the sample are denatured, separated using one-dimensional SDS gel electrophoresis, and transferred onto a support membrane and immobilized thereon using the Western blot method.

After biotinylation of the immobilized proteins, this matrix is then cut into columns approximately 1 cm in width and 5-10 cm in length and containing all the proteins of the sample. Thereafter, the columns are cut into 0.5 mm wide strips. From each individual strip, the protein is then eluted and bound in each case to distinguishable bead populations. Sufficient protein is eluted from each strip to coat several thousand microspheres. The signal is then generated in a direct bead-based immunoassay, which requires about 100 microspheres per assay. Thus, several hundred assays can be carried out using the microspheres generated from one fraction.

In view of the above, it is preferred if, in step a), the biological sample is separated by gel electrophoresis and the resulting band pattern is transferred preferably onto a matrix, wherein preferably the biomolecules/proteins transferred onto the matrix are modified, preferably biotinylated, for binding to a support molecule such as avidin or streptavidin and, if further preferably in step a), the matrix is mechanically divided into small segments and the biomolecules are thereafter eluted from the individual segments into respective fractions, wherein preferably the matrix is cut into at least one column and the at least one column is cut into multiple strips, wherein the at least one column is cut into at least 10, preferably 20 to 200, strips.

The advantage of this gel electrophoretic separation over a column-based method is that many samples can be separated in parallel at the same time. A further advantage is the simple and cost-effective implementation of the gel-based method. In addition, the biomolecules bound to the matrix can be biotinylated more effectively than the biomolecules present in fractions after a column separation.

While it is also possible to mechanically divide the gel itself, i.e., to cut it into columns and strips, this mechanical manipulation can be carried out more easily and more reproducibly in the case of a matrix, more particularly in the case of a matrix used in a Western blot.

As a result of the mechanical division of gel or matrix, the biomolecules/proteins/peptides separated according to physical property in the bands are distributed onto the segments/strips and spatially separated from one another.

It is not necessary to stain the gel after the separation since the resulting bands do not have to be visible for the further course of the new method. Checking whether the separation was successful can be carried out at the level of the microspheres.

We therefore provide methods capable of detecting different biomolecules present in a complex sample using a multiplex immunoassay.

It is preferred if, in step b), the biomolecule-coated microspheres from at least several fractions are mixed together to form a master mix and preferably this master mix is then divided up into aliquots and, if further preferably in step b), a specific binding molecule, preferably an antibody, is added to at least one aliquot, wherein the binding molecule is designed to emit a preferably optically detectable signal, wherein further preferably, in step b), the intensity of the detectable signal is determined for the biomolecules from an aliquot and separately according to the microsphere populations.

From the master mix, many aliquots can be taken, each of which are tested against an antibody.

The proteins can, in step a), be denatured prior to the electrophoretic separation, wherein the biological sample in step a) can be pretreated prior to the electrophoretic separation to degrade the proteins into peptide fragments and, so, in step b), the peptide fragments are detected.

The biolomecules from some or all fractions may be further processed in step a) such that each processed fraction gives at least rise to one fraction in a first set of fractions and preferably one further fraction in a second set of fractions, the biomolecules in the first and the second set of fractions differing according to posttranslational protein modification, preferably the processing includes enrichment of biomolecules showing one type of posttranslational modification in the fractions of the first set and further preferably a depletion of biomolecules showing the one type of posttranslational modification in the fractions of the second set, further preferably in step b), the biomolecule-coated microspheres from some or all fractions of one set are mixed together to form a master mix.

This has to be seen against the background of posttranslational modifications of proteins that frequently determine the function of a protein. Therefore, it is advantageous for new methods of detecting biomolecules to be able to distinguish between modified and unmodified proteins.

However, for many posttranslational modifications, there are no specific binding molecules available that selectively either bind the modified or the unmodified protein. But, what is available are binding agents that generically bind to many different proteins carrying a specific modification.

Posttranslational modifications include among others acetylation, phosphorylation, methylation, prenylation, ubiquitinylation, sumoylation, glycosylation, o-N-acetylglcosa-minylation. A more complete list of modifications can be found on the Wikipedia website under "Posttranslational_modification."

Agents generically binding to different proteins having the same modification include antibodies against such structures (e.g., anti-acetyllysine antibodies for recognizing acetylated proteins), binding proteins that recognize specific sugars (e.g., lectins), immobilized ions to enrich phosphorylated proteins (e.g., gallium oxide-coated magnetic microspheres).

The biomolecules, after having been fractionated in step a), can be further fractionated according to their type of posttranslational modifications such that a first set of fractions is enriched with biomolecules having a specific posttranslational modification. Preferably, a second set is depleted from biomolecules having the modification. To this end, several or all fractions obtained in step a) can be further processed by affinity enrichment methods using agents that generically bind biomolecules having a specific type of posttranslational modification, but do not distinguish between different proteins having the same modification.

After that further processing, the one or two sets of fractions further proceed as described above. The fractions from each set are loaded on microspheres specific for each fraction, pooled into a master mix, and each master mix is divided up into aliquots.

When now a protein-specific antibody is added to the aliquots of each set of fractions, one can discern from comparing the optical read-out of both sets the amount of modified and unmodified protein in the original sample.

This has the advantage that selected proteins having a specific posttranslational modification can be analyzed although no binding molecules are available that specifically bind to such selected proteins that carry such modification.

Since with our methods a great number of different protein-specific antibodies can be used with fractions obtained from one gel electrophoresis run, from one small biological sample many such proteins can be analyzed for posttranslational modification although no antibodies are available that specifically bind to proteins having the modification.

We surprisingly found that the fluorescent signal obtained in each case for the different physical property values, i.e., for the individual fractions, is higher when the strip has been cut out more narrowly from the matrix. Therefore, resolution of the mechanical division affects the sensitivity of the methods.

It is possible to carry out a large number of measurements using a small amount of sample material. Using 10 µg of protein, as is typically used for detection of a protein in a Western blot, it is possible to create a master mix with which hundreds of measurements can be carried out.

From 20 000 to 50 000 cells or 5 to 20 µg of cellular protein, it is possible according to our initial experiments to detect a few dozen to several hundred different proteins.

It is possible to bind, for example, up to 96 different antibodies to the material from a Western blot lane after aliquoting. Hence, up to a thousand measurements are possible. This allows a comprehensive characterization of the material studied. Thus, the study of cellular signal transduction such as the phosphorylation cascades is possible.

Our new methods also exhibit very good resolution. A Western blot lane can, for example, be divided up into up to 96 fractions. Thus, proteins present in various isoforms of different molecular weight, processed proteins and modified proteins can be distinguished and can be detected using an antibody.

Because of the fractionation of the proteins using gel electrophoresis, increased use of nonspecific antibodies is also now possible.

Furthermore, our systems have a good dynamic range because specific signals are summed from positive fractions. Experiments with different antibodies revealed that a dynamic range of over 10 000 with good linearity is possible.

Spike-in experiments with recombinant fusion proteins showed that the quantification of an intrinsic protein with this internal standard is possible.

By mixing samples immobilized on different bead populations and measuring the mixed samples in one reaction, a comparative measurement of different samples and an internal standardization are possible. This is especially relevant because in this way tumor tissue and normal tissue, or tumor tissue before and after a treatment, can be compared in a single measurement.

Use of our methods is especially interesting in the case of limiting sample amounts, for example, when clinical tumor material or tumor cell populations obtained following laser capture microdissection. Thus, tumor markers can be detected and an analysis of signal transduction can be carried out.

In addition, our methods can be used in the analysis of modified proteins. For example, in the context of phosphoproteomics, phosphorylation can be detected. In addition, epigenetic changes such as histone modifications can be detected.

Especially surprising in this combination of two detection methods is that the signal-to-noise ratio in the analysis of the loaded microspheres is better when the cut-out bands are narrower since the narrower the cut-out band, the "purer" the eluted protein.

The biotinylation of the proteins bound on the membrane allows even small amounts of protein to be immobilized on the microspheres. The result of the extremely high affinity of the biotin-streptavidin interaction is that streptavidin beads can be loaded even with little material and a good coating density is achieved.

Further advantages are apparent from the description and the attached drawings.

It will be appreciated that the features mentioned above and those to be explained below are usable not only in the combination indicated in each case, but also in other combinations or alone, without departing from the scope of this disclosure.

Our methods are described below by examples, which are explained by the figures.

EXAMPLE 1: Detection of Proteins from Small Amounts of Biological Material

FIGS. 1A to H show simplistically, starting from A, essential steps of our methods.

First, the proteins present in a complex biological sample are denatured according to a customary protocol.

Thereafter, the proteins are separated according to molecular weight by gel electrophoresis on an SDS gel (FIG. 1A). This band pattern is then, as in the case of a Western blot, transferred onto a protein-binding membrane (FIG. 1B).

The proteins now bound on the membrane are modified by the introduction of biotin (FIG. 1C). The protein bands are now present in multiple columns next to one another. One of these columns is now mechanically cut out of the membrane and cut into many narrow strips (FIG. 1D).

Seen in the longitudinal direction of the columns, the strips are so short that one protein band can split up over several adjacent strips.

From each strip, the protein is then eluted into an aqueous solution. 20 to 200 fractions are generated from one membrane strip (FIG. 1E).

To each fraction is then added a distinguishably color-coded microsphere population, with each microsphere having a streptavidin coating. Hence, the protein is immobilized on the microspheres (FIG. 1F). This generates 20 to 200 microsphere populations loaded with protein from different strips and distinguishable via their color coding.

These microsphere populations are then first mixed together, whereupon the mixture is then divided into up to 500 aliquots. Each aliquot contains at least 100 microspheres from each fraction. To each aliquot is added a specific antibody which specifically binds to one of the proteins to be detected in the complex sample (FIG. 1G).

These antibodies are, for example, fluorescently labelled. Therefore, a particular protein can be identified and quantified via the combination of the measurement values for the color signal (identification of the strip) and the fluorescent signal (protein recognized) and the summing of the fluorescent signals for each microsphere population.

If the fluorescent summed signal is displayed against the fractions identified via the microsphere populations, i.e., against molecular weight, then what are specific (shaded in FIG. 1H) can be distinguished from what are unspecific (pale in FIG. 1H) and quantified.

Between the steps of FIGS. 1E and F, the biomolecules in several or all fractions can be subjected to affinity enrichment for a certain posttranslational modification. By this, from each so processed fraction there is produced one fraction having enriched all biomolecules showing the posttranslational modification. Further, a second fraction may be obtained wherein biomolecules carrying the modification are depleted.

Enrichment can be performed by incubating the initial fraction with an immobilized binding reagent (e.g., a generic modification specific antibody) and thereby the initial fraction is depleted from biomolecules carrying this modification. By an elution step modified biomolecules get released and are found to be enriched in a new fraction. The process can be repeated sequentially for different posttranslational modifications.

This produces a first set of fractions with biomolecules carrying the modification being enriched and, preferably a second set, wherein the biomolecules carrying the modification are depleted.

Each set of fractions is further processed, as detailed above, by adding microspheres, pooling the fractions into a master mix and dividing the master mix into various aliquots.

By adding protein-specific antibodies to each aliquot, one can now analyze from the first set of fractions the proteins carry the modification. Further, by comparing the related fractions from the first and second set, one can at least semi-quantitatively determine the ratio of modified proteins.

EXAMPLE 2: Detection of ERK1 and ERK2 in Human Liver Cell Lines

15 μg of protein extract from a human liver cell line (HepG2) were tested using the method shown in FIG. 1 for the presence of the proteins ERK1 and ERK2 following SDS gel electrophoresis in the Western blot.

A first antibody which recognizes the proteins ERK1 and ERK2 was used in a first analysis (A). A second antibody which recognizes phosphorylated ERK1 and ERK2 was used in a second analysis (B).

The fluorescent summed signals for 96 bead populations were measured, which had been coated in each case with proteins eluted from the membrane strips. For the measurement, all 96 bead populations were mixed and 100 000 beads, i.e., about 1000 beads per population, were incubated with antibodies.

FIG. 2 shows two bar charts featuring the measured signal intensities and the photo of a blot strip which had been developed in a standard Western blot.

The two proteins can be distinguished and quantified.

EXAMPLE 3: Quantification of ERK1 in Human Liver Cell Lines

20 μg of cell lysate from the human liver cell line HepG2 were applied in each case in 4 lanes on an SDS polyacrylamide gel.

To the first sample were added 20 ng of purified GST-ERK1 fusion protein, to the next sample 4 ng, then 0.8 ng, then 0.16 ng. Following electrophoretic separation, the proteins were transferred onto a membrane and modified using biotin.

The four individual lanes were each subsequently cut into 60 strips and the proteins dissolved from the surface of the strips. The eluates generated from the individual strips were immobilized on 60 distinguishable microsphere populations and pooled to form a master mix.

Thus, in this experiment, there were 4 batches containing equal amounts of HepG2 cell lysate (and thus also contained equal amounts of intrinsic ERK1 and ERK2) but different, defined amounts of GST-ERK1 fusion protein.

As a result of incubation of the 4 samples with a specific anti-ERK antibody, it was possible to generate measurement signals (relative fluorescence intensity) for ERK1, ERK2 and the GST-ERK1 fusion protein. For the measurement, 100 000 beads, which corresponds to about 1000 beads per population, were incubated with the ERK1/2-specific antibody. The signals for the known amounts of the fusion protein were used to create a standard curve, and the curve was used to calculate the absolute amount of ERK1.

The bar chart in FIG. 3A shows signals for the HepG2 sample containing 4 ng of GST-ERK1 fusion protein; peaks at molecular weight 65 kDa, 42 kDa and 39 kDa correspond to GST-ERK1, ERK2 and ERK1.

The right-hand side of FIG. 3B shows the relative fluorescence intensity of the intrinsic ERK1 in the 4 lanes.

EXAMPLE 4: Analysis of Tumor Material Present in a Limited Amount

Frozen tumor tissue was cut and histologically assessed. In the examined sections, it was possible to identify two histologically distinguishable tumor regions.

Using laser microdissection, approximately 20 000 cells were taken from both regions. The contained proteins were solubilized in detergent-containing lysis buffer.

For both tumor regions, the method according to FIG. 1 was used to separate the proteins by gel electrophoresis according to size and 96 protein fractions were generated in each case. The fractions for the two tumor regions were immobilized on 192 distinguishable bead populations. These were combined for the measurement. Thus, it was possible for both samples to be tested comparatively in one assay for differences in protein expression.

The major advantage of our methods is the number of analyses now possible. Using the 20 000 cells available, up to 200 assays can be carried out. Using a customary Western blot, only 1-8 assays can be carried out with this material.

Expression of 54 proteins was studied in a comparative analysis. For the majority of the analytes studied (45/54), no noticeable changes in expression between the samples were detected; see FIG. 4, where again the fluorescent summed signals are shown against molecular weight.

Figure 4:
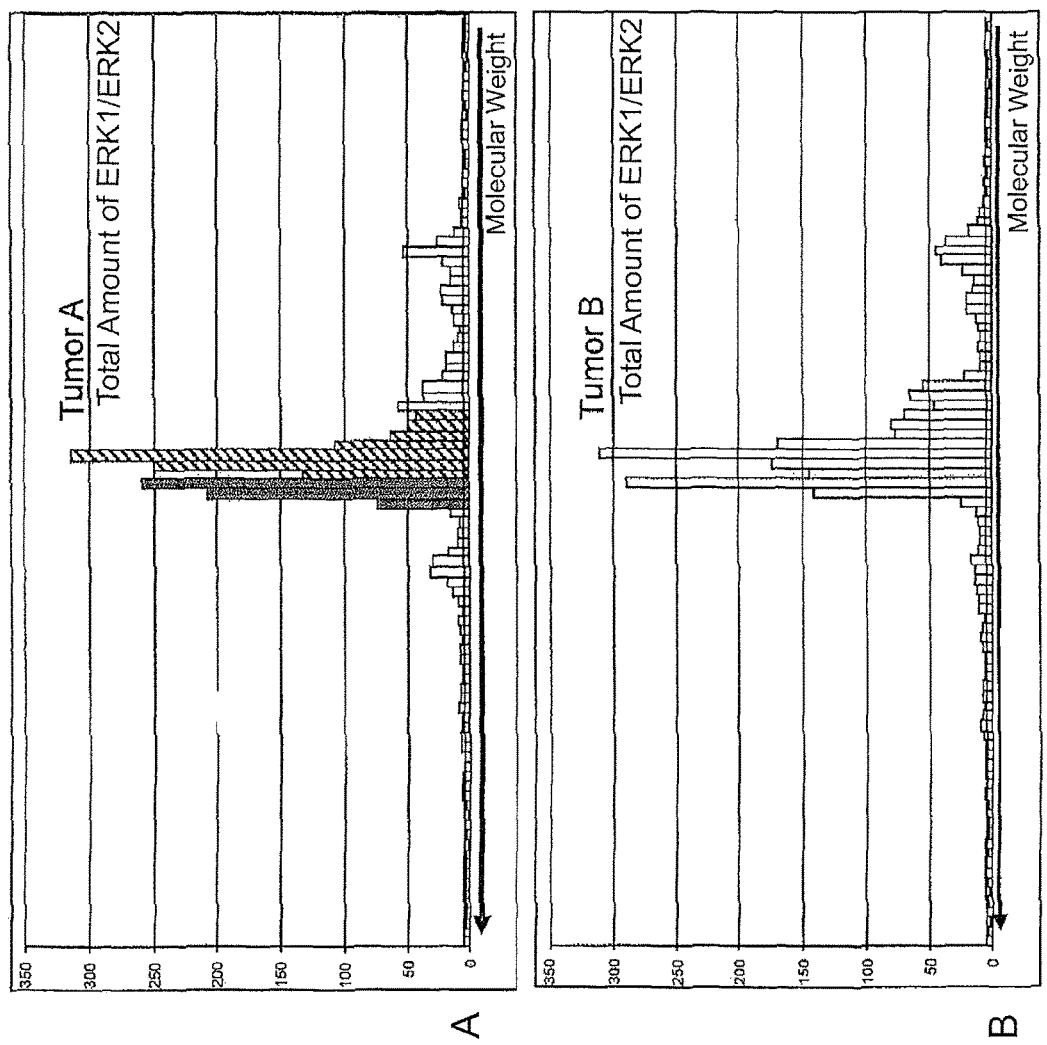
FIGS. 4A and B show two bar charts concerning the detection of ERK1/ERK2 in tumor tissue.

It can be seen from FIG. 4 that it is possible to detect the expression of the total amount of ERK1 (hatched bars) and ERK2 (grey bars) using an ERK1/2-specific antibody. Both proteins are detectable; differences in expression between the kinases were not found.

Significant changes were detected for a minority of the analytes. Of particular significance is the detection of the activation of a central regulator of cellular growth.

Figure 5A:
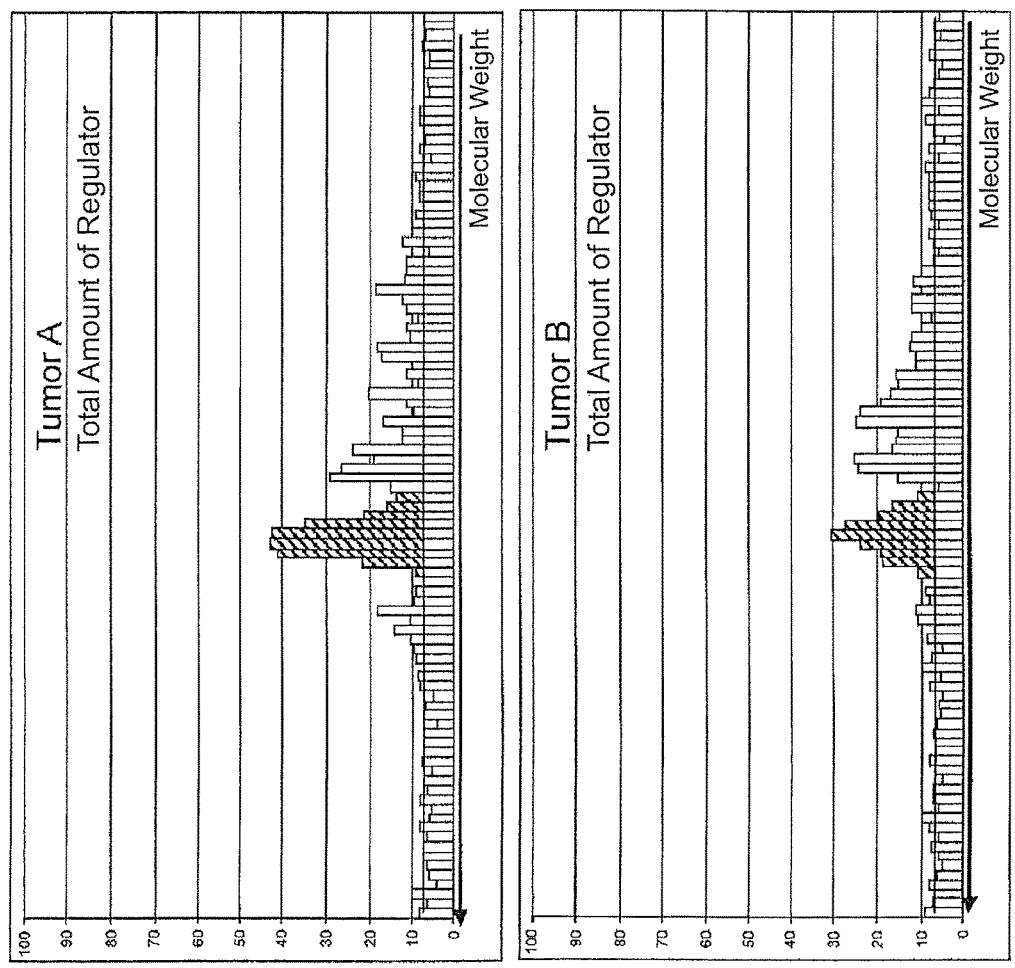
FIGS. 5A and B each show two bar charts concerning detection of the activation of a regulator in two different tumor tissues.

Using a specific antibody, the expression of the total amount of the regulator from tumor A and tumor B was determined; see FIG. 5A.

Figure 5B:
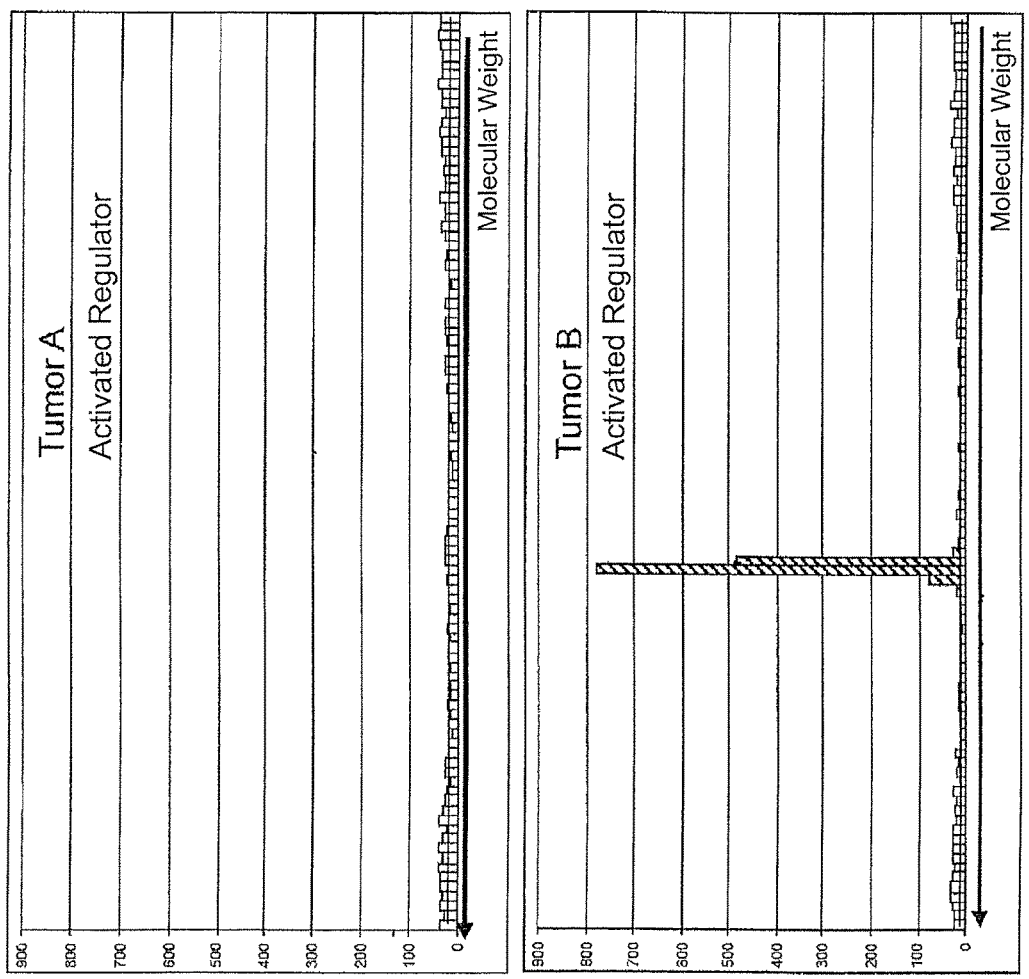

Using an activation-specific antibody, the amount of activated regulator was further determined; see FIG. 5B. This revealed a ratio of 83:1 for tumor B:tumor A.

The invention claimed is:

1. A method of detecting biomolecules present in a complex biological sample comprising:
   a) separating the biological sample into fractions according to at least one physical property of the biomolecules; and
   b) specifically detecing biomolecules present in the fractions using at least one solid-phase-based, immunological detection method including immobilizing the biomolecules from the individual fractions on microsphere populations specific for each fraction and distinguishable from one another.

2. The method according to claim 1, wherein, in step a), the biological sample is separated by gel electrophoresis.

3. The method according to claim 2, wherein, in step a), the resulting band pattern is transferred onto a matrix.

4. The method according to claim 3, wherein the separated biomolecules are modified to bind to a support molecule.

5. The method according to claim 3, wherein, in step a), the matrix is mechanically divided into small segments and the biomolecules are thereafter eluted from the individual segments into respective fractions.

6. The method according to claim 5, wherein the matrix is cut into at least one column and the at least one column is cut into multiple strips and the biomolecules are thereafter eluted from the individual strips into respective fractions.

7. The method according to claim 6, wherein the at least one column is cut into at least 10 strips.

8. The method according to claim 1, wherein in step a) the biomolecules from some or all fractions are further processed such that each processed fraction gives rise to at least one fraction in a first set of fractions and at least one fraction in a second set of fractions, the biomolecules in the first and the second set of fractions differing according to posttranslational protein modification.

9. The method according to claim 8, wherein the processing includes enrichment of biomolecules showing one type of posttranslational modification in the fractions of the first set and a depletion of biomolecules showing said one type of posttranslational modification in the fractions of the second set.

10. The method according to claim 8, wherein, in step b), the biomolecule-coated microspheres from some or all fractions of one set are mixed together to form a master mix.

11. The method according to claim 1, wherein, in step b), the biomolecule-coated microspheres from some or all fractions are mixed together to form a master mix.

12. The method according to claim 11, wherein, in step b), the master mix is divided into aliquots.

13. The method according to claim 12, wherein, in step b), a specific binding molecule such as an antibody is added to at least one aliquot, wherein the binding molecule is designed to emit an optically detectable signal.

14. The method according to claim 13, wherein, in step b), intensity of the detectable signal is determined for the biomolecules from an aliquot and separately according to the microsphere populations.

15. The method according to claim 1, wherein the biomolecules in step a) are denatured prior to the electrophoretic separation.

16. The method according to claim 1, wherein the biomolecules are proteins.

17. The method according to claim 16, wherein the biological sample in step a) is pretreated prior to separation to degrade the proteins into peptide fragments and in step b) the peptide fragments are detected.

18. The method according to claim 4, wherein the separated biomolecules are biotinylated to bind to a support molecule.

19. The method according to claim 4, wherein the support molecule is avidin or streptavidin.

* * * * *